(12) United States Patent
Allen et al.

(10) Patent No.: US 7,078,528 B2
(45) Date of Patent: Jul. 18, 2006

(54) BIIMIDAZOLE DIAMIDE ANION BINDING AGENTS

(75) Inventors: William E. Allen, Greenville, NC (US); Corey P. Causey, Durham, NC (US)

(73) Assignee: East Carolina University, Greenville, NC (US)

( * ) Notice: Subject to any disclaimer, the term of this patent is extended or adjusted under 35 U.S.C. 154(b) by 258 days.

(21) Appl. No.: 10/612,447

(22) Filed: Jul. 2, 2003

(65) Prior Publication Data

US 2005/0004370 A1  Jan. 6, 2005

(51) Int. Cl.
*C07D 403/02* (2006.01)

(52) U.S. Cl. ............... 548/313.1; 548/313.4; 436/518

(58) Field of Classification Search .............. 548/313.1, 548/313.4
See application file for complete search history.

(56) References Cited

U.S. PATENT DOCUMENTS 5,593,593 A  1/1997  Nilsen et al.

OTHER PUBLICATIONS

Beer et al., Anion Recognition and Sensing: The State of the Art and Future Perspectives, *Angew. Chem. Int. Ed.*, 40:486-516 (2001).

Causey et al., Anion Binding by Fluorescent Biimidazole Diamides, *J. Org. Chem.*, 67:5963-5968, Aug. 23, 2002.

Fortin et al., Preparation and Characterization of Oxorhenium (V) complexes with 2,2'-Biimidazole: The Strong Affinity of Coordinated Biimidazole for Chloride Ions via N-H . . . Cl⁻ Hydrogen Bonding, *Inorg. Chem.*, 39:4886-4893 (2000).

Gale et al., 2-Amidopyrroles and 2,5-Diamidopyrroles as Simple Anion Binding Agents, *J. Org. Chem.*, 66:7849-7853 (2001).

Schmidtchen et al., Artificial Organic Host Molecules for Anions, *Chem. Rev.*, 97:1609-1646 (1997).

*Primary Examiner*—Laura L. Stockton
(74) *Attorney, Agent, or Firm*—Myers Bigel Sibley & Sajovec, PA

(57) ABSTRACT

Biimidazole diamide compounds that are useful for binding anions such as sulfate are described, along with the use thereof for purposes such as extracting anions from a waste stream and/or detecting anions.

5 Claims, 2 Drawing Sheets

BIIMIDAZOLE DIAMIDE ANION BINDING AGENTS

FIELD OF THE INVENTION

The present invention concerns anion binding agents and methods of use thereof.

BACKGROUND OF THE INVENTION

Artificial receptors that are capable of selectively binding anionic species show promise in the diagnosis and treatment of diseases and in environmental remediation (Beer, P. D.; Gale, P. A. *Angew. Chem. Int. Ed.* 2001, 40, 486; Gale, P. A. *Coord. Chem. Rev.* 2000, 199, 181; Snowden, T. S.; Anslyn, E. V. *Curr. Opin. Chem. Biol.* 1999, 3, 740; Antonisse, M. M. G.; Reinhoudt, D. N. *Chem. Commun.* 1998, 443; Beer, P. D. *Acc. Chem. Res.* 1998, 31, 71; Schmidtchen, F. P.; Berger, M. *Chem. Rev.* 1997, 97, 1609). For example, sensors for inorganic phosphate could be used to monitor ATP synthesis/hydrolysis or kinase-dependent cell signaling. "Carrier" molecules can also enhance through-membrane transport of chloride ion, which is a goal of cystic fibrosis research. Anion binding species may also be used in the extraction of nitrate from rivers and lakes, which is expected to inhibit eutrophication, and the associated oxygen depletion and fish kills. In addition, extraction of anions from nuclear waste prior to vitrification may decrease nuclear waste volume.

Several anion receptors have been constructed from 5-membered heterocycles (Sessler, J. L.; Davis, J. M. *Acc. Chem. Res.* 2001, 34, 989; Cafeo, G.; Kohnke, F. H.; La Torre, G. L.; White, A. J. P.; Williams, D. J. *Chem. Commun.* 2000, 1207; Anzenbacher, P., Jr.; Jursíková, K.; Sessler, J. L. *J. Am. Chem. Soc.* 2000, 122, 9350; Miyaji, H.; Sato, W.; Sessler, J. L. *Angew. Chem. Int. Ed.* 2000, 39, 1777; Sessler, J. L.; Allen, W. E. *CHEMTECH* 1999, 29, 16; Sato, K.; Arai, S.; Yamagishi, T. *Tetrahedron Lett.* 1999, 40, 5219), (thio)amides (Ayling, A. J.; Pérez-Payán, M. N.; Davis, A. P. *J. Am. Chem. Soc.* 2001, 123, 12716; Choi, K.; Hamilton, A. D. *J. Am. Chem. Soc.* 2001, 123, 2456; Miyaji, H.; Sessler, J. L. *Angew. Chem. Int. Ed.* 2001, 40, 154; Jagessar, R. C.; Burns, D. H. *Chem. Commun.* 1997, 1685), or both (Gale, P. A.; Camiolo, S.; Tizzard, G. J.; Chapman, C. P.; Light, M. E.; Coles, S. J.; Hursthouse, M. B. *J. Org. Chem.* 2001, 66, 7849), because these groups form relatively strong NH-anion hydrogen bonds. Previous work has also established that coupling luminescent moieties to H-bond donors can yield sensors that operate at low anion concentrations (Liao, J.-H.; Chen, C.-T.; Fang, J.-M. *Org. Lett.* 2002, 4, 561; Gunnlaugsson, T.; Davis, A. P.; Glynn, M. *Chem. Commun.* 2001, 2556; Sun, S.-S.; Lees, A. J. *Chem. Commun.* 2000, 1687; Beer, P. D.; Szemes, F.; Balzani, V.; Salà, C. M.; Drew, M. G. B.; Dent, S. W.; Maestri, M. *J. Am. Chem. Soc.* 1997, 119, 11864). We describe here a series of anion receptors that incorporate all of these features into a single molecular unit (Sessler, J. L.; Maeda, H.; Mizuno, T.; Lynch, V. M.; Furuta, H. *Chem. Commun.* 2002, 862; Anzenbacher, P., Jr.; Try, A. C.; Miyaji, H.; Jursikova, K.; Lynch, V. M.; Marquez, M.; Sessler, J. L. *J. Am. Chem. Soc.* 2000, 122, 10268; Black, C. B.; Andrioletti, B.; Try, A. C.; Ruiperez, C.; Sessler, J. L. *J. Am. Chem. Soc.* 1999, 121, 10438). Specifically, electrically neutral biimidazole diamides are shown to simultaneously serve as multiple H-bond donors (Fortin, S.; Beauchamp, A. L. *Inorg. Chem.* 2000, 39, 4886) and as anion-sensitive fluorophores.

SUMMARY OF THE INVENTION

A first aspect of the present invention is a compound of Formula I:

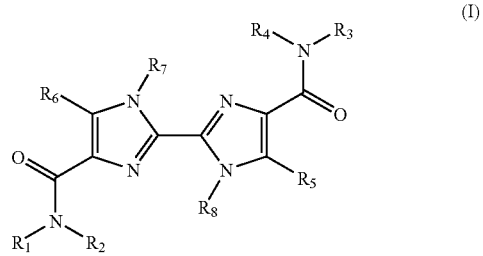

wherein:

$R_1$, $R_2$, $R_3$ and $R_4$ are each independently H, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, alkoxy, substituted alkoxy, arylalkenyl, substituted arylalkenyl, arylalkynyl, substituted arylalkynyl, aroyl, acyl, heterocyclic, substituted heterocyclic, halogen, cyano, nitro, macrocyclic ligand, and lipophilic groups;

$R_5$ and $R_6$ are each independently H, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, alkoxy, substituted alkoxy, arylalkenyl, substituted arylalkenyl, arylalkynyl, substituted arylalkynyl, aroyl, acyl, heterocyclic, substituted heterocyclic, halogen, cyano, nitro, or a macrocyclic ligand; and $R_7$ and $R_8$ are each independently H or lower alkyl.

In one embodiment of the foregoing, wherein at least one (e.g., one, two, three, four) of $R_1$, $R_2$, $R_3$ and $R_4$ is a macrocyclic ligand.

In one embodiment of the foregoing, wherein at least one (e.g., one, two, three, four) of $R_1$, $R_2$, $R_3$ and $R_4$ is a lipophilic group.

A further aspect of the present invention is a compound as described above immobilized on a solid support.

A further aspect of the present invention is a compound as described above, further comprising an anion such as sulfate bound thereto (useful for purposes such as an intermediate in a purification or vitrification process).

A further aspect of the present invention is a method of binding an anion such as sulfate, comprising contacting an anion to a compound as described above so that said anion is bound thereto.

A further aspect of the present invention is a method of extracting an anion from a mixed composition containing the same, comprising the steps of: (a) contacting said mixed composition to a binding compound of Formula I as described above so that said anion is bound thereto; and then (b) separating said binding compound from said mixed composition to thereby extract said anion from said mixed composition. In one embodiment the mixed composition comprises nuclear waste material, and the method further comprising the step of vitrifying the mixed composition following said separating step. In one embodiment of the foregoing method, the binding step is immobilized on a solid support so that it may be easily separated from the mixed composition prior to the subsequent vitrification step.

A further aspect of the present invention is a method of detecting an anion, comprising the steps of: (a) contacting an anion to a binding compound of Formula I as described herein; and then (b) determining (e.g. by fluorometry) the fluorescence of said compound, wherein said compound is less fluorescent when said anion is bound thereto, to thereby detect said anion. The contacting step may be carried out by any suitable means, such as by combining the anion and the compound in a common liquid solution (e.g., a solution comprising or consisting essentially of dichloromethane).

The present invention is explained in greater detail in the drawings herein and the specification set forth below.

DETAILED DESCRIPTION OF THE PREFERRED EMBODIMENTS

Figure 1:
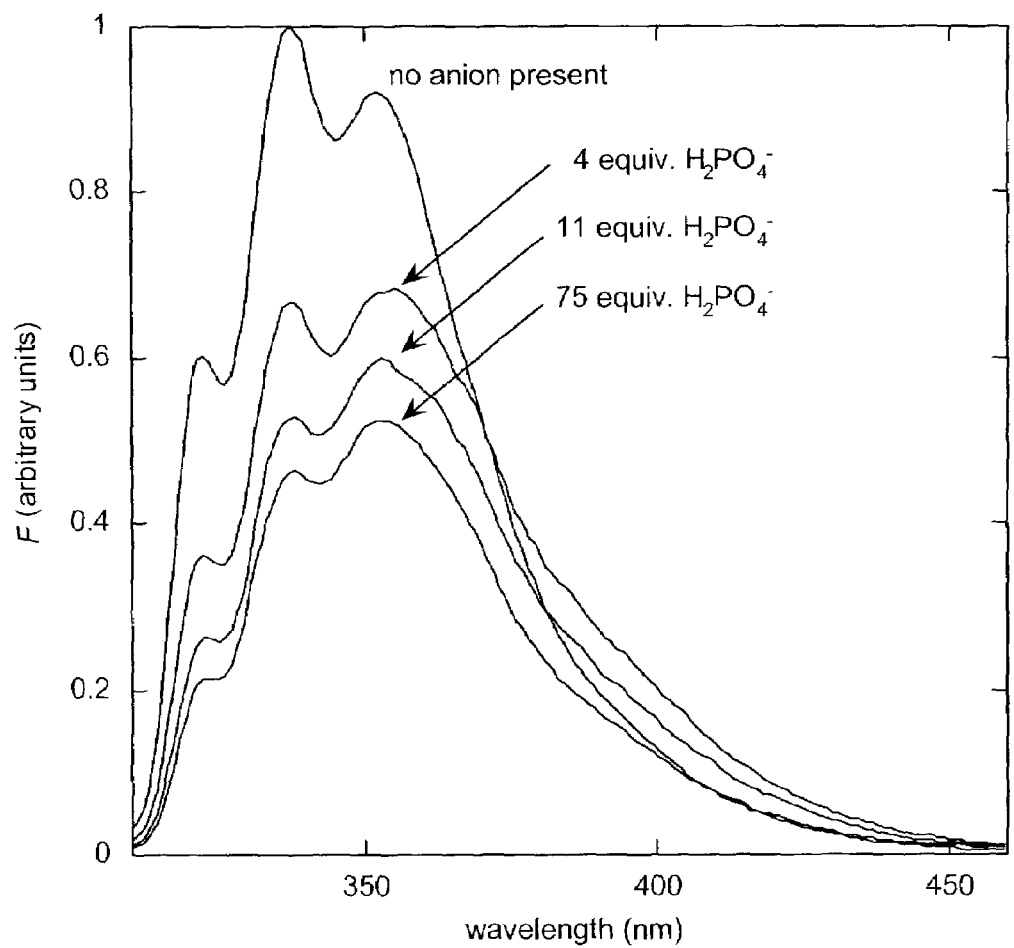
FIG. 1 shows representative emission spectra for 1c ($2.5 \times 10^{-6}$ M) in aerated $CH_2Cl_2$ during titration with $Bu_4N^+$ $H_2PO_4^-$. $\lambda_{excit}$=300 nm.
Figure 2:
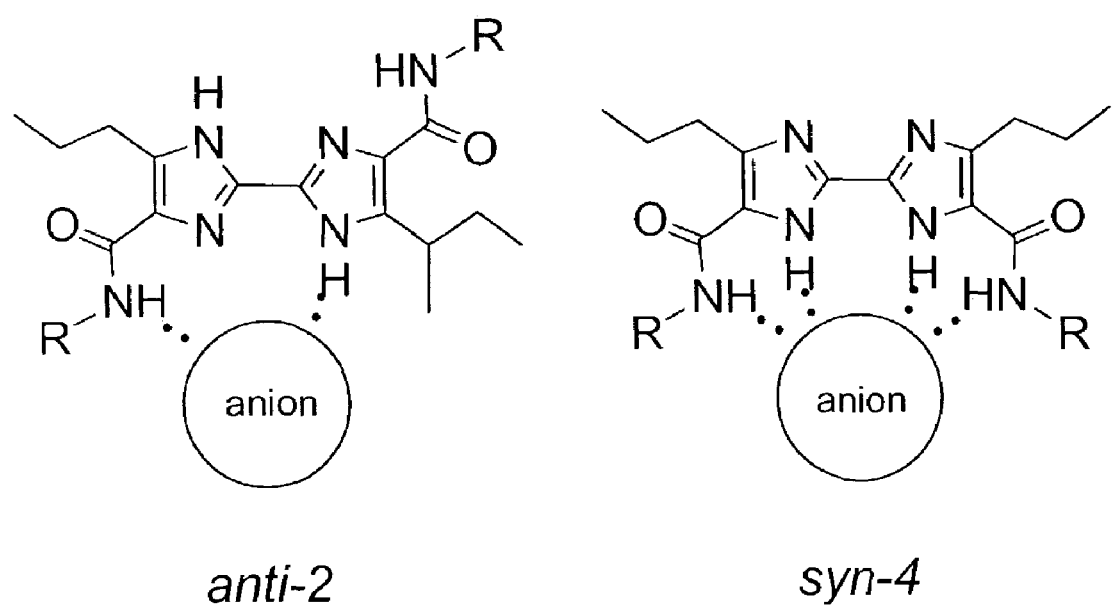
FIG. 2 shows possible structures of biimidazole—anion complexes.

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

This invention discloses a compound of the general structure of Formula I.

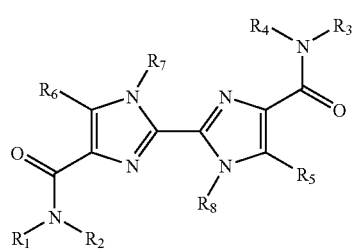

Formula I

When discussed herein, the term "lower alkyl" refers to straight or branched chain alkyl radicals having in the range of about 1 up to 4 carbon atoms;

"alkyl" refers to linear or branched chain alkyl radicals having in the range of about 1 up to about 12 carbon atoms, including methyl, ethyl, propyl, butyl, pentyl, hexyl, septyl, octyl, nonyl, decyl, undecyl and dodecyl;

"substituted alkyl" refers to alkyl radicals further bearing one or more substituents such as hydroxyl, alkoxy (of a lower alkyl group), mercapto (of a lower alkyl group), halogen, trifluoromethyl, cyano, nitro, amino, carboxyl, carbamate, sulfonyl, sulfonamide, and the like;

"cycloalkyl" refers to cyclic ring-containing radicals containing in the range of about 3 up to 8 carbon atoms, and "substituted cycloalkyl" refers to cycloalkyl radicals further bearing one or more substituents as set forth above;

"alkenyl" refers to straight or branched chain hydrocarbyl radicals having at least one carbon-carbon double bond, and having in the range of about 2 up to 12 carbon atoms, and "substituted alkenyl" refers to alkenyl radicals further bearing one or more substituents as set forth above;

"alkynyl" refers to straight or branched chain hydrocarbyl radicals having at least one carbon-carbon triple bond, and having in the range of about 2 up to 12 carbon atoms, and "substituted alkynyl" refers to alkynyl radicals further bearing one or more substituents as set forth above;

"aryl" refers to aromatic radicals having in the range of 6 up to 14 carbon atoms, and "substituted aryl" refers to aryl radicals further bearing one or more substituents as set forth above;

"alkylaryl" refers to alkyl-substituted aryl radicals, and "substituted alkylaryl" refers to alkylaryl radicals further bearing one or more substituents as set forth above;

"arylalkyl" refers to aryl-substituted alkyl radicals, and "substituted arylalkyl" refers to arylalkyl radicals further bearing one or more substituents as set forth above;

"alkoxy" refers to an alkoxy radical having in the range of 1 up to 12 carbon atoms, and "substituted alkoxy" refers to alkoxy radicals further bearing one or more substituents as set forth above;

"arylalkenyl" refers to aryl-substituted alkenyl radicals, and "substituted arylalkenyl" refers to arylalkenyl radicals further bearing one or more substituents as set forth above;

"arylalkynyl" refers to aryl-substituted alkynyl radicals, and "substituted arylalkynyl" refers to arylalkynyl radicals further bearing one or more substituents as set forth above;

"aroyl" refers to aryl-carbony species such as benzoyl, and "substituted aroyl" refers to aroyl radicals further bearing one or more substituents as set forth above;

"heterocyclic" refers to cyclic (i.e. ring containing) radicals containing one or more heteroatoms (e.g., N, O, S, or the like) as part of the ring structure and having in the range of 3 up to 14 carbon atoms, and "substituted heterocyclic" refers to heterocyclic radicals further bearing one or more substituents as set forth above;

"acyl" refers to alkyl-carbony species;

"halogen" refers to fluoride, chloride, bromide or iodide radicals;

"anion" refers to any negatively charged ion, including but not limited to $Cl^-$, $SO_4^{--}$, and $H_2PO_4^-$; and The term "macrocyclic ligand" as used herein means a macrocyclic molecule of repeating units of carbon atoms and heteroatoms (e.g., O, S, or NH), separated by the carbon atoms (generally by at least two or three carbon atoms). Macrocyclic ligands exhibit a conformation with a so-called hole capable of trapping ions or molecules, particularly cations, by coordination with the electrons of the heteroatom (e.g., a lone pair of electrons on the oxygen atoms when the heteroatoms are oxygen). In general, the macrocyclic ring contains at least 9, 12 or 14 carbon atoms and heteroatoms (e.g. O, S, NH), each heteroatom in the ring being separated from adjoining heteroatoms in the ring by two or more carbon atoms. The macrocyclic ring may be substituted or unsubstituted, and may be fused to additional rings (e.g., 1 to 4 additional rings such as phenylene, naphthylene, phenanthrylene, and anthrylene rings).

The term "crown ether" as used herein means a macrocyclic polyether whose structure exhibits a conformation with a so-called hole capable of trapping cations by coordination with a lone pair of electrons on the oxygen atoms (*McGraw-Hill Dictionary of Scientific and Technical Terms* (3d ed. 1984)). Crown ethers are a species of macrocyclic ligand.

The present invention may be carried out by substituting at least one hetero atom of a macrocyclic ligand or crown ether with a 1,4-phenylenediamine group by covalent bond to one, or both, of the amine nitrogen atoms.

Any macrocyclic ligand or crown ether can be substituted as shown herein and used to carry out the present invention, including but not limited to those described in U.S. Pat. Nos. 5,252,733; 5,589,446; 5,587,499; 5,536,577; 5,478,953; 5,391,628; 4,876,367; 4,777,270; 4,652,399; 4,254,034; 4,104,275; 4,031,111; 4,024,158; 4,001,279; 3,997,562; 3,997,565; 3,987,061; and 3,687,978; the disclosures of which applicants specifically intend to be incorporated herein by reference in their entirety. The term "macrocyclic ligand" as used herein encompasses macrobicyclic ligands as well. Examples of redox active macrocyclic ligands of the present invention are compounds of Formula II:

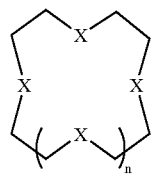

Formula II wherein X is O, S, or NH and n is 1, 2 or 3 to 6, 10, 20, 30 or 40. Preferably, X is O.

In Formula II, the C2 alkylene groups shown between hetero atoms X may be replaced with different alkylene groups (e.g., C3 or C4 alkylene groups). All of the alkylene groups in the ring system may be the same, or they may differ. The resulting ring system may be symmetric or asymmetric. The alkylene groups may be unsubstituted or substituted (e.g., they may be substituted with any of the groups shown in the patents incorporated by reference above).

An advantage of the use of macrocyclic ligands is that they can bind and/or extract an additional cation such as a sodium or potassium ion concurrently with the binding of an anion such as sulfate, where such an additional binding capability is desired.

As noted above, one or more of $R_1$, $R_2$, $R_3$ and/or $R_4$ may be a lipophilic group. Examples of compounds incorporating such lipophilic groups include but are not limited to the following:

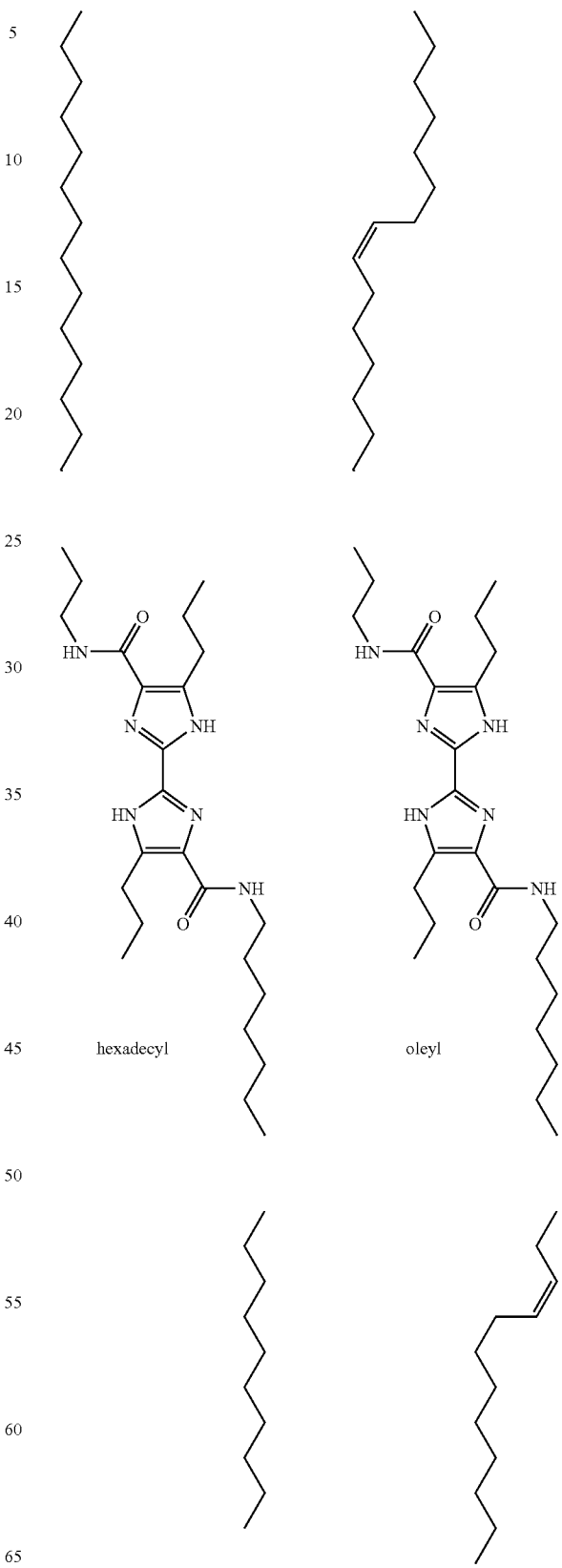

hexadecyl oleyl

One procedure for the synthesis of the biimidazoles is shown in Scheme I. In the first step, an ester, such as the ester 2, is hydrolyzed to a carboxylic acid with concentrated aqueous HCl at reflux (Paul, R.; Brockman, J. A.; Hallett, W. A.; Hanifin, J. W.; Tarrant, M. E.; Torley, L. W.; Callahan, F. M.; Fabio, P. F.; Johnson, B. D.; Lenhard, R. H.; Schaub, R. E.; Wissner, A. *J. Med. Chem.* 1985, 28, 1704). The carboxylic acid is then converted to the corresponding acid chloride by reaction with excess oxalyl chloride in solvent at reflux (Collman, J. P.; Bröring, M.; Fu, L.; Rapta, M.; Schwenninger, R. *J. Org. Chem.* 1998, 63, 8084). Amides (such as compounds 5a–f) are prepared by treating an acid chloride (such as compound 4) with a series of amines. Removal of excess amine followed by recrystallization or column chromatography affords the desired amides. Installation of a halogen at the imidazole 2-position of the amides, required for subsequent biimidazole bond formation, is accomplished by treating the amides with N-iodosuccinimide (NIS) (Allen, W. E.; Fowler, C. J.; Lynch, V. M.; Sessler, J. L. *Chem. Eur. J.* 2001, 7, 721). In the final step of the synthesis, a palladium(0)-promoted homocoupling reaction is employed. Iodides, such as 6a–f, are treated with N,N-diisopropylethylamine and a catalytic amount of Pd(PPh$_3$)$_4$ to yield the biimidazole compounds.

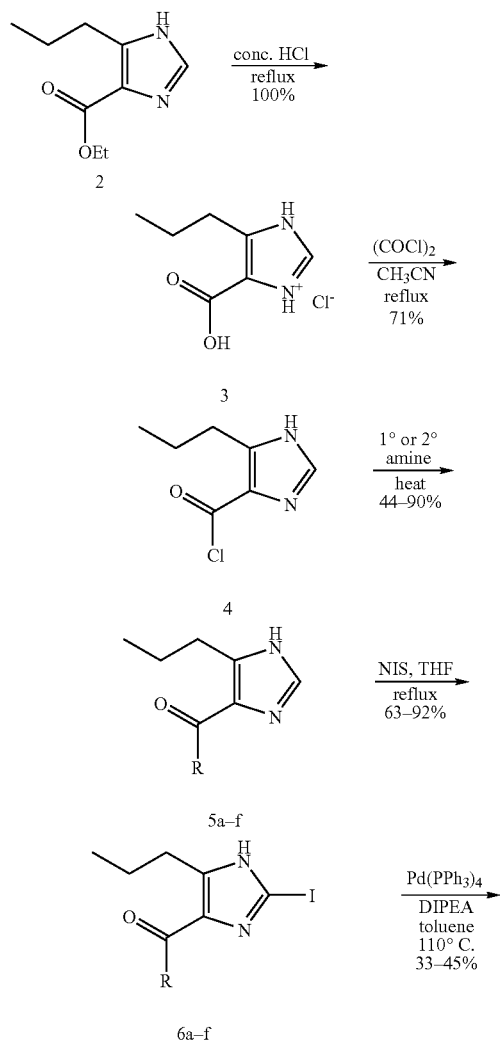

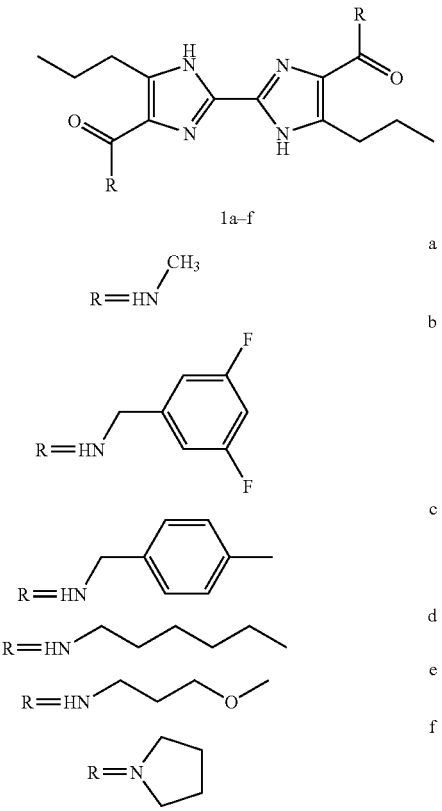

Compounds of the present invention may be immobilized on a solid support by any of a variety of routine techniques. For example, commercially available polystyrene resins that are functionalized with phenolic groups can be used in conjunction with a biimidazole bearing a COOH group to covalently couple the biimidazole to the resin using a carbodiimide coupling agent an an amine base in a solvent such as DMF.

The removal of anions from waste streams can be achieved by a number of different methods. One such method involves mixing the biimidazole with a waste mixture to allow binding of the anion to the biimidazole. Then, the waste mixture is selectively extracted to remove the compound/anion complex from the mixture. Another method is to immobilize the claimed compound onto a solid support and then mix the supported compound with the waste mixture, thereby trapping the anions. Then, the solid supports may be washed and filtered to remove the waste mixture. A subsequent step can include washing the solid supported anion complexes with a solvent that removes the anionic species, thereby recovering the anion species and leaving the supported biimidazoles available for re-use.

Fluorescence detection can be carried out in accordance with any suitable technique such as with a fluorometer or scintillation counter.

Separation of an anion such as a sulfate for vitrification can be carried out with binding agents of the present invention utilized in conjunction with known techniques (see, e.g., U.S. Pat. No. 5,593,493 to Nilsen et al.). When used for vitrification of a waste mixture, it will be appreciated that the binding compound, being organic, may degrade during the vitrification process and potentially release sulfate into the glass. Therefore, the anion/binding compound conjugate or combination is preferably removed or separated from the waste mixture prior to vitrification (e.g., by immobilizing the binding compound to a solid support and contacting the waste mixture to the solid support in a batch or continuous separation process).

The present invention is explained in greater detail in the following non-limiting Examples.

EXAMPLE 1

5-Propyl-1H-imidazole-4-carboxylic acid hydrochloride (3)

5-Propyl-1H-imidazole-4-carboxylic acid ethyl ester 2 (2.00 g; 11.0 mmol) and concentrated aqueous HCl (40 mL) were combined and heated to reflux with stirring for 24 h. After cooling to rt, the light tan solution was diluted with water (100 mL) and extracted with EtOAc. The aqueous layer was then evaporated under reduced pressure. The residue was dissolved in 2-propanol (20 mL) and cooled to −78 C. Upon addition of $Et_2O$, a white precipitate formed. This material was collected by filtration and dried under vacuum to afford 2.10 g (100%) of 3. $^1$H NMR (DMSO-$d_6$): δ 0.87 (t, 3H), 1.69 (m, 2H), 2.92 (t, 2H), 9.17 (s, 1H); $^{13}$C NMR (DMSO-$d_6$): δ 13.9, 22.4, 26.4, 120.9, 135.7, 140.0, 160.7; Anal. calcd for $C_7H_{11}ClN_2O_2 0.66(C_3H_9O)0.33$ ($H_2O$): C, 45.67; H, 7.24; N, 11.84; Cl, 14.98; found: C, 45.27; H, 7.17; N, 11.86; Cl, 14.68.

EXAMPLE 2

5-Propyl-1H-imidazole-4-carbonyl chloride (4)

5-Propyl-1H-imidazole-4-carboxylic acid hydrochloride 3 (1.0 g; 5.3 mmol) was added to nitrogen-purged $CH_3CN$ (10 mL). Oxalyl chloride (2.5 ml; 29 mmol) was then added, and the mixture was heated to reflux under $N_2$ for 1 h. The brown solution was then allowed to cool, and the product began to precipitate. Ice-cold dry $Et_2O$ (30 mL) was added to the reaction flask to complete the precipitation. The green-gold solid was collected by suction filtration, washed with $Et_2O$, and dried under vacuum to afford 0.65 g (71%) of 4. $^1$H NMR (DMSO-$d_6$): δ 0.90 (t, 3H), 1.70 (m, 2H), 2.90 (t, 2H), 8.70 (s, 1H); $^{13}$C NMR (DMSO-$d_6$): δ 13.6, 21.3, 29.4, 118.1, 137.9, 150.46, 155.8.

EXAMPLE 3

General Procedure for Preparation of Amides 5a–f

Under $N_2$, a round-bottomed flask containing a stir bar was charged with 5-propyl-1H-imidazole-4-carbonyl chloride 4 (0.40 g, 2.3 mmol) and 3–4 mL of a neat liquid amine. The mixture was stirred with gentle warming from a heat gun for 5 minutes, during which time a cloud of white vapor appeared in the flask. The mixture was partitioned between 100 mL of water and 100 mL of an organic solvent ($CH_2Cl_2$ or EtOAc-THF (1:1, v:v), as required for solubility). The organic phase was then washed with saturated aqueous NaCl and was dried over $Na_2SO_4$ or $MgSO_4$, as appropriate. Filtration, rotary evaporation of the filtrate, and drying for 24 h under high vacuum afforded the crude amide as a yellow-orange oil or solid. Further purification was performed as described below.

EXAMPLE 4

5-Propyl-1H-imidazole-4-carboxylic acid methylamide (5a)

Using a solution of 40% aqueous methylamine, 0.31 g (80%) of amide 5a was obtained as colorless prisrms after recrystallization from $CH_3CN—CH_3OH$. mp 173–175 ÿC; 1H NMR ($CD_3OD$): δ 0.97 (t, 3H), 1.65 (m, 2H), 2.55 and 2.90 (both s, 3H total), 2.95 (t, 2H), 7.50 (s, 1H), 7.85 (br t, 1H); $^{13}$C NMR ($CD_3OD$): δ 14.0, 23.8, 25.8, 27.8, 135.0, 137.7, 166.7; LRMS (CI+): m/z (%): 168 (100), [M+H]+; HRMS (CI+): calcd for $C_8H_{14}N_3O$ 168.1137; found 168.1141.

EXAMPLE 5

5-Propyl-1H-imidazole-4-carboxylic acid 3,5-difluorobenzylamide (5b)

Using 3,5-difluorobenzylamine, crude amide 5b was obtained as a viscous yellow oil after flash column chromatography on silica gel using EtOAc as the eluent. Recrystallization from $Et_2O$-hexanes afforded 0.32 g (50%) of pure 5b as colorless needles. mp 104–105 ÿC; TLC (EtOAc): $R_f$=0.33; $^1$H NMR ($CDCl_3$): δ 0.95 (t, 3H), 1.63 (m, 2H), 2.97 (t, 2H), 4.59 (d, 2H), 6.60 (t, 1H), 6.80 (d, 2H), 7.32 (s, 1H), 8.00 (br t, 1H); $^{13}$C NMR ($CDCl_3$): δ 13.8, 22.8, 27.2, 42.2, 110.0, 129.5, 133.4, 137.2, 143.1, 161.8, 164.7; LRMS (CI+): m/z (%): 280 (100), [M+H]+; HRMS (CI+): calcd for $C_{14}H_{16}F_2N_3O$ 280.1261; found 280:.263; Anal. calcd for $C_{14}H_{15}N_3O$: C, 60.21, H, 5.41, N, 15.05; found: C, 60.21; H, 5.43, N, 14.98.

EXAMPLE 6

5-Propyl-1H-imidazole-4-carboxylic acid 4-methylbenzylamide (5c)

Using 4-methylbenzylamine, 0.53 g (90%) of amide 5c was obtained as an off-white solid after flash column chromatography on silica gel using EtOAc as the eluent. mp 131–133 ÿC; TLC (EtOAc): $R_f$-0.28; $^1$H NMR ($CDCl_3$): δ 0.85 (t, 3H), 1.65 (m, 2H), 2.30 (s, 3H), 3.00 (t, 2H), 4.57 (d, 2H), 7.10 (dd, 4H), 7.25 (s, 1H), 7.62 (br t, 1H); $^{13}$C NMR ($CDCl_3$): δ 13.9, 21.7, 22.5, 27.1, 43.0, 133.6, 135.8, 137.7, 164.8; LRMS (CI+): m/z (%): 258 (100), [M+H]+; HRMS (CI+): calcd for $C_{15}H_{20}N_3O$ 258.1606; found 258.1600.

EXAMPLE 7

5-Propyl-1H-imidazole-4-carboxylic acid hexylamide (5d)

Using 1-hexylamine, 0.49 g (90%) of amide 5d was obtained as light yellow plates after recrystallization from $CH_3CN$. mp 103–104 ÿC; $^1$H NMR ($CDCl_3$): δ 0.87 (br t, 6H), 1.30 (m, 6H), 1.61 (m, 2H), 1.65 (m, 2H), 3.00 (t, 2H), 3.37 (q, 2H), 7.22 (br t, 1H), 7.48 (s, 1H); $^{13}$C NMR ($CDCl_3$): δ 14.1, 14.2, 22.8, 22.9, 27.2, 30.0, 31.3, 31.8, 39.1, 132.8, 136.0, 164.2; LRMS (CI+): m/z (%): 238 (100), [M+H]+; HRMS (CI+): calcd for $C_{13}H_{24}N_3O$ 238.1919; found 238.1912; Anal. calcd for $C_{13}H_{23}N_3O$: C, 65.79; H, 9.77; N, 17.70; found: C, 65.89; H, 9.38; N, 17.72.

EXAMPLE 8

5-Propyl-1H-imidazole-4-carboxylic acid (3-methoxypropyl)amide (5e)

Using 3-methoxypropylamine, 0.44 g (85%) of amide 5e was obtained as yellow crystals after flash column chromatography using EtOAc—$CH_3OH$ (9:1, v:v) as the eluent. mp 61–63 ÿC; TLC (EtOAc—$CH_3OH$, 9:1): $R_f$=0.30; $^1H$ NMR ($CDCl_3$): δ 0.82 (t, 3H), 1.55 (m, 2H), 1.75 (m, 2H), 2.90 (t, 2H), 3.21 (s, 3H), 3.40 (m, 4H), 7.35 (s, 1H), 7.44 (br t, 1H); $^{13}C$ NMR ($CDCl_3$): δ 13.9, 23.7, 27.7, 30.5, 37.3, 58.9, 71.5, 134.1, 138.3, 164.6; LRMS (CI+): m/z (%): 226 (100), [M+H]+; HRMS (CI+): calcd for $C_{11}H_{20}N_3O_2$ 226.1556; found 226.1553.

EXAMPLE 9

(5-Propyl-1H-imidazol-4-yl)-pyrrolidin-1-yl-methanone (5f)

Using pyrrolidine, 0.21 g (44%) of amide 5f was obtained as yellow needles after recrystallization from $CH_3CN$. mp 121–122 ÿC; $^1H$ NMR ($CDCl_3$): δ 0.85 (t, 3H), 1.61 (m, 2H), 1.90 (br m, 4H), 2.84 (t, 2H), 3.60 (br s, 2H), 3.90 (br s, 2H), 7.40 (s, 1H); $^{13}C$ NMR ($CDCl_3$): δ 13.5, 22.5, 23.8, 44.9, 46.3, 46.7, 48.8, 131.0, 136.5, 164.5; LRMS (CI+): m/z (%): 208 (100), [M+H]+; HRMS (CI+): calcd for $C_{11}H_{18}N_3O$ 208.1450; found 208.1445; Anal. calcd for $C_{11}H_{17}N_3O$: C, 63.74; H, 8.27; N, 20.27; found: C, 63.57; H, 8.30; N, 20.26.

EXAMPLE 10

General Procedure for Preparation of 2-Iodo Amides 6a-f

An imidazole amide 5 (1–2 mmol) was dissolved in dry THF (25 mL) in a round-bottomed flask containing a stir bar. N-Iodosuccinimide (NIS) (2.0 equiv.) was added in one portion, and the flask was covered with foil to exclude light. The mixture was heated to reflux for 24 h under $N_2$, then was allowed to cool to rt. Saturated aqueous $NaHSO_3$ (7 mL) was added dropwise to destroy the excess iodine reagent. The solvents were removed under reduced pressure, and the residue was partitioned between water and an organic solvent ($CHCl_3$ or EtOAc, as determined by solubility). The organic phase was dried over $Na_2SO_4$, filtered, and the filtrate was evaporated to yield the 2-iodo product as a solid. In most cases, this crude material was used in the subsequent Pd(0)-coupling step without additional purification.

EXAMPLE 11

2-Iodo-5-propyl-1H-imidazole-4-carboxylic acid methylamide (6a)

Starting from 5a (0.30 g; 1.8 mmol), 0.45 g (87%) of 6a was obtained as a yellow solid. 1H NMR ($CD_3OD$): δ 0.89 (t, 3H), 1.61 (m, 2H), 2.63 and 2.82 (both s, 3H total), 2.91 (t, 2H), 7.85 (s, 1H); $^{13}C$ NMR ($CD_3OD$): δ 13.9, 23.7, 25.9, 27.7, 134.5, 142.0, 165.3; LRMS (CI+): m/z (%): 294 (100), [M+H]+; HRMS (CI+): calcd for $C_8H_{13}IN_3O$ 294.0103; found 294.0010.

EXAMPLE 12

2-Iodo-5-propyl-1H-imidazole-4-carboxylic acid 3,5-difluorobenzylamide (6b)

Starting from 5b (0.32 g; 1.1 mmol), 0.39 g (84%) of 6b was obtained as yellow solid. $^1H$ NMR ($CDCl_3$): δ 0.91 (t, 3H), 1.62 (m, 2H), 2.99 (t, 2H), 4.58 (d, 2H), 6.68 (t, 1H), 6.84 (d, 2H), 7.64 (br t, 1H), 9.14 (br s, 1H); $^{13}C$ NMR ($CDCl_3$): δ 13.9, 22.8, 27.1, 42.3, 110.5, 133.8, 141.7, 143.0, 161.6, 163.0, 165.1; LRMS (CI+): m/z (%): 406 (100), [M+H]+; HRMS (CI+): calcd for $C_{14}H_{15}F_2IN_3O$ 406.0228; found 406.0219.

EXAMPLE 13

2-Iodo-5-propyl-1H-imidazole-4-carboxylic acid 4-methylbenzylamide (6c)

Starting from 5c (0.30 g; 1.2 mmol), 0.38 g (85%) of 6c was obtained as a yellow solid. $^1H$ NMR ($CDCl_3$): δ 0.93 (t, 3H), 1.64 (m, 2H), 2.33 (s, 3H), 3.01 (t, 2H), 4.56 (d, 2H), 7.17 (dd, 4H), 7.40 (br t, 1H); $^{13}C$ NMR ($CDCl_3$): δ 14.0, 21.3, 22.8, 29.8, 42.9, 128.1, 129.5, 135.6, 137.1, 141.0, 162.5; LRMS (CI+): m/z (%): 290 (100), 384 (10), [M+H]+; HRMS (CI+): calcd for $C_{15}H19IN_3O$ 384.0573; found 384.0585.

EXAMPLE 14

2-Iodo-5-propyl-1H-imidazole-4-carboxylic acid hexylamide (6d)

Starting from 5d (0.30 g; 1.3 mmol), 0.42 g (92%) of 6d was obtained as a yellow solid. 1H NMR ($CDCl_3$): δ 0.81 (br t, 6H), 1.23 (m, 6H), 1.57 (m, 4H), 2.96 (t, 2H), 3.35 (q, 2H), 7.16 (br t, 1H), 11.39 (br s, 1H); $^{13}C$ NMR ($CDCl_3$): δ 13.7, 14.0, 22.6, 26.7, 26.9, 29.6, 31.5, 39.0, 134.0, 140.8, 162.5; LRMS (CI+): m/z (%): 364 (100), [M+H]+; HRMS (CI+): calcd for $C_{13}H_{23}IN_3O$ 364.0886; found 364.0877.

EXAMPLE 15

2-Iodo-5-propyl-1H-imidazole-4-carboxylic acid (3-methoxypropyl)amide (6e)

Starting from 5e (0.56 g; 2.5 mmol), the crude product obtained from the General Procedure was further purified by flash column chromatography on silica gel using EtOAc as the eluent. Fractions containing the fast spot were combined and evaporated to afford 0.55 g (63%) of 6e as a white solid. TLC (EtOAc): $R_f$=0.48; $^1H$ NMR ($CD_3OD$): δ 0.80 (t, 3H), 1.52 (m, 2H), 1.76 (m, 2H), 2.85 (t, 2H), 3.23 (s, 3H), 3.29 (m, 2H), 3.37 (t, 2H), 7.70 (br t, 1H); $^{13}C$ NMR ($CD_3OD$): δ 13.9, 23.7, 27.7, 30.5, 58.9, 71.5, 134.5, 142.1, 164.6; LRMS (CI+): m/z (%): 352 (100), [M+H]+; HRMS (CI+): calcd for $C_{11}H_{19}IN_3O_2$ 352.0522; found 352.0528.

EXAMPLE 16

(2-Iodo-5-propyl-1H-imidazol-4-yl)-pyrrolidin-1-yl-methanone (6f)

Starting from 5f (0.21 g; 1.0 mmol), 0.30 g (89%) of 6f was obtained as a yellow solid. $^1H$ NMR ($CDCl_3$): δ 0.89 (t, 3H), 1.60 (m, 2H), 1.90 (br m, 4H), 2.80 (t, 2H), 3.61 (br s, 2H), 3.85 (br s, 2H), 9.30 (s, 1H); $^{13}C$ NMR ($CDCl_3$): δ 13.7, 21.0, 22.6, 23.9, 26.4, 46.6, 49.0, 136.5, 141.9, 163.0; LRMS (CI+): m/z (%): 334 (100), [M+H]+; HRMS (CI+): calcd for $C_{11}H_{17}IN_3O$ 334.0416; found 334.0419.

EXAMPLE 17

General Procedure for Preparation of Biimidazole Diamides 1a–f

An iodide 6 (1.0–1.6 mmol) and dry toluene (30 mL) were placed in a thick-walled pressure tube containing a stir bar. The solution was purged with $N_2$ for 5 min, then N,N-diisopropylethylamine (2.0 equiv) and tetrakis (triphenylphosphine) palladium(0) (0.040 equiv) were added to the reaction mixture. The tube was sealed, covered in foil, and heated at 110 C for 48 h, during which time the reaction turned dark red-brown. Subsequent isolation and purification of products 1a–f varied, as described below.

EXAMPLE 18

5,5'-Dipropyl-1H,1'H-[2,2']biimidazolyl-4,4'-dicarboxylic acid bis(methylamide) (1a)

Iodide 6a (0.35 g; 1.2 mmol) was used as starting material. After cooling to rt, the reaction mixture was diluted with $CH_3OH$ and filtered. The filtrate was evaporated under vacuum, and the residue was dissolved in $CH_2Cl_2$. Upon standing, a white solid precipitated. This material was collected by filtration and was washed with ice-cold $CH_2Cl_2$ to afford 0.080 g (43%) of 1a. mp>260 ÿC; TLC (EtOAc): $R_f$=0.32; 1H NMR (DMSO-$d_6$): δ 0.83 (t, 6H), 1.61 (m, 4H), 2.73 (d, 6H), 2.89 (t, 4H), 7.50 (br t, 2H); $^{13}C$ NMR (DMSO-$d_6$): δ 13.1, 21.9, 24.7, 30.2, 130.3, 135.6, 163.0; UV/vis ($CH_3OH$): $\lambda_{max}$ (ε $M^{-1}cm^{-1}$)=286 (18500), 294 (18200), 309 (9860); Anal. calcd for $C_{16}H_{24}N_6O_2 \cdot 0.25$ ($CH_2Cl_2$): C, 55.19; H, 6.98; N, 23.76; found: C, 54.93; H, 6.71; N, 23.74.

EXAMPLE 19

5,5'-Dipropyl-1H,1'H-[2,2']biimidazolyl-4,4'-dicarboxylic acid bis(3,5-difluorobenzylamide) (1b)

Iodide 6b (0.44 g; 1.1 mmol) was used as starting material. After cooling to rt, the reaction mixture was diluted with $CH_3OH$ and filtered. The filtrate was evaporated under vacuum, and the residue was dissolved in $CHCl_3$. Slow addition of $CH_3CN$ caused a brown solid to precipitate. This material was collected by filtration and washed with $CH_3CN$ to afford 0.12 g (40%) of 1b as an off-white solid. mp 173–174 C; TLC ($CH_2Cl_2$-EtOAc, 1:1): $R_f$=0.51; $^1H$ NMR (DMSO-$d_6$): δ 0.85 (t, 6H), 1.60 (m, 4H), 2.90 (t, 4H), 4.42 (d, 4H), 6.99 (d, 4H), 7.05 (t, 2H), 8.20 (br t, 2H); $^{13}C$ NMR (DMSO-$d_6$): δ 14.1, 23.1, 30.2, 41.8, 110.9, 131.0, 141.7, 145.5, 161.3, 163.8, 164.7; UV/vis ($CH_3OH$): $_{max}$ ($M^{-1}cm^{-1}$)=287 (21800), 294 (20700), 309 (10700); LRMS (CI+): m/z (%): 557 (100) [M+H]+; HRMS (CI+): calcd for $C_{28}H_{29}F_4N_6O_2$ 557.2288; found 557.2292.

EXAMPLE 20

5,5'-Dipropyl-1H,1'H-[2,2']biimidazolyl-4,4'-dicarboxylic acid bis(4-methylbenzylamide) (1c)

Iodide 6c (0.45 g; 1.2 mmol) was used as starting material. After cooling to rt, the reaction mixture was diluted with $CH_3OH$ and filtered. The filtrate was evaporated under vacuum, and the residue was triturated with $CH_3CN$. The solid that remained undissolved was collected by filtration and washed with $CH_3CN$ to afford 0.30 g (38%) of 1c as an off-white microcrystalline solid. An analytical sample was recrystallized from $CH_3OH$. mp 226–227 C; TLC ($CH_2Cl_2$-EtOAc, 1:1): $R_f$=0.60; $^1H$ NMR ($CD_2Cl_2$): δ 0.80 (t, 6H), 1.59 (m, 4H), 2.21 (s, 6H), 2.86 (t, 4H), 4.39 (d, 4H), 7.05 (dd, 8H), 7.22 (br t, 2H); $^{13}C$ NMR (DMSO-$d_6$): δ 14.2, 21.4, 23.3, 27.0, 49.6, 128.3, 129.9, 131.0, 137.0, 138.7, 164.2; UV/vis ($CH_3OH$): $_{max}$ ($M^{-1}cm^{-1}$)=287 (25100), 295 (25100), 310 (13700); LRMS (CI+): m/z (%): 513 (100) [M+H]+; HRMS (CI+): calcd for $C_{30}H_{37}N_6O_2$ 513.2978; found 513.2981; Anal. calcd for $C_{30}H_{36}N_6O_2 \cdot 0.33(H_2O)$: C, 68.68; H, 7.17; N, 16.02; found: C, 68.58; H, 7.17; N, 16,11.

EXAMPLE 21

5,5'-Dipropyl-1H,1'H-[2,2']biimidazolyl-4,4'-dicarboxylic acid bis(hexylamide) (1d)

Iodide 6d (0.45 g; 1.1 mmol) was used as starting material. After cooling to rt, the reaction mixture was diluted with $CH_3OH$ and filtered. The filtrate was evaporated under vacuum, and the residue was recrystallized from $CH_3OH$ to afford 0.12 g (45%) of 1d as a white solid. mp>260 C; TLC ($CH_2Cl_2$-EtOAc, 1:1): $R_f$=0.51; $^1H$ NMR ($CDCl_3$): δ 0.88 (br t, 6H), 0.97 (t, 6H), 1.31 (br m, 12H), 1.60 (m, 4H), 1.72 (m, 4H), 3.06 (t, 4H), 3.38 (q, 4H), 7.00 (br t, 2H); $^{13}C$ NMR (DMSO-$d_6$): δ 14.2, 14.6, 22.8, 23.1, 26.9, 30.2, 31.7, 38.7, 131.3, 137.2, 163.5; UV/vis ($CH_3OH$): $_{max}$ ($M^{-1}cm^{-1}$)=287 (26000), 295 (25900), 309 (14100); LRMS (CI+): m/z (%): 473 (100) [M+H]+; HRMS (CI+): calcd for $C_{26}H_{45}N_6O_2$ 473.3604; found 473.3601; Anal. calcd for $C_{26}H_{44}N_6O_2$: C, 66.07; H, 9.38; N, 17.78; found: C, 66.26; H, 9.54; N, 17.83.

EXAMPLE 22

5,5'-Dipropyl-1H,1'H-[2,2']biimidazolyi-4,4'-dicarboxylic acid bis[(3-methoxypropyl)amide] (1e)

Iodide 6e (0.55 g; 1.6 mmol) was used as starting material. After cooling to rt, the reaction mixture was diluted with $CH_3OH$ and filtered. The filtrate was evaporated under vacuum, and the residue was recrystallized from EtOAc to afford 0.13 g (33%) of 1e as colorless prisms. mp>260 C; TLC (EtOAc): $R_f$=0.31; $^1H$ NMR ($CDCl_3$): δ 0.91 (t, 6H), 1.65 (m, 4H), 1.82 (m, 44), 3.00 (t, 4H), 3.34 (s, 6H), 3.48 (m, 8H), 7.29 (br t, 2H); $^{13}C$ NMR (DMSO-$d_6$): δ 14.3, 24.1, 26.7, 32.3, 61.9, 72.3, 137.5, 145.1, 167.3; UV/vis ($CH_3OH$): $_{max}$ ($M^{-1}cm^{-1}$)=287 (25600), 295 (25400), 309 (13800); LRMS (CI+): m/z (%): 449 (100) [M+H]+; HRMS (CI+): calcd for $C_{22}H_{37}N_6O_4$ 449.2876; found 449.2875; Anal. calcd for $C_{22}H_{36}N_6O_4$: C, 58.91; H, 8.09; N, 18.74; found: C, 59.00; H, 8.09; N, 18.78.

EXAMPLE 23

[5,5'-Dipropyl-4'-(pyrrolidine-1-carbonyl)-1H, 1'H-[2,2']biimidazolyl-4-yl]-pyrrolidin-1-yl-methanone (1f)

Iodide 6f (0.34 g; 1.0 mmol) was used as starting material. After cooling to rt, the reaction mixture was diluted with $CH_3OH$ and filtered. The filtrate was evaporated under vacuum, and the residue was recrystallized from $CH_3OH$ to afford 0.080 g (38%) of 1f as yellow prisms. mp>260 C;

TLC (EtOAc): $R_f$=0.14; $^1$H NMR (DMSO-$d_6$): δ 0.84 (t, 6H), 1.59 (m, 4H), 1.80 (br m, 8H), 2.80 (t, 4H), 3.55 (br m, 4H), 3.90 (br m, 4H); $^{13}$C NMR (DMSO-$d_6$): δ 14.3, 23.4, 24.2, 26.9, 31.4, 46.8, 49.0, 132.9, 138.0, 163.7; UV/vis (CH$_3$OH): $_{max}$ (M$^{31}$ $^1$cm$^{-1}$)=287 (21200), 294 (20900), 309 (sh); LRMS (CI+): m/z (%): 208 (100), 413 (70) [M+H]+; HRMS (CI+): calcd for C$_{22}$H$_{33}$N$_6$O$_2$ 413.2665; found 413.2662; Anal. calcd for C$_{22}$H$_{32}$N$_6$O$_2$0.33(H$_2$O): C, 63.13; H, 7.87; N, 20.08; found: C, 63.21; H, 7.82; N, 20.08.

EXAMPLE 24

Fluorescence Titrations

Biimidazole diamides 1b–f were dissolved in spectrophotometric grade dichloromethane such that the concentration of each solution was between 1×10$^{-6}$ M and 3×10$^{-6}$ M (sonication was required to effect complete dissolution in some cases). An electronic absorption spectrum was acquired for each sample to ensure that the optical density was less than 0.1. A 3.0 mL sample of biimidazole diamide solution was transferred to a quartz cuvette and placed into the fluorometer. The sample was excited at 300 nm, and an emission spectrum from 310–460 nm was recorded. Upon completion of the scan, the area contained under the emission band (F) was computed. Aliquots of an approximately 0.03 M solution of anion (as tetrabutylammonium (Bu$_4$N$^+$) salt) in CH$_2$Cl$_2$ were then injected into the sample solution through a small hole in the cap. The sample solution was magnetically stirred for 1 min after each addition, then was scanned again. This process was repeated until the change in fluorescence intensity became insignificant. The total volume of the sample solution changed by less than 2% over the course of the experiment.

Binding constants ($K_{assoc}$) were derived from plots of F/F$_0$ vs. [anion] (Connors, K. A. *Binding Constants*, Wiley, N.Y., 1987). During iterative fitting to the equation F/F$_0$= (1+($k_{complex}$/$k_{biimid}$)$K_{assoc}$[anion])/(1+$K_{assoc}$[anion]), the values of $k_{complex}$ and $K_{assoc}$ were allowed to vary freely. The constant $k_{biimid}$ is equal to F$_0$/[biimid]$_0$. Results reported in Table 1 are averages of at least two replicate titrations.

TABLE 1

Binding Constants, $K_{assoc}$ (M$^{-1}$) for 1b-f with Dihydrogenphosphate and Chloride in CH$_2$Cl$_2$ at 23° C.

| biimidazole | H$_2$PO$_4^-$ | Cl$^-$ |
| --- | --- | --- |
| 1b | 6.8 × 10$^4$ | 1.4 × 10$^5$ |
| 1c | 4.6 × 10$^4$ | 3.7 × 10$^4$ |
| 1d | 4.7 × 10$^4$ | 2.7 × 10$^4$ |
| 1e | 4.1 × 10$^4$ | 2.5 × 10$^4$ |
| 1f | 2.0 × 10$^4$ | 4.0 × 10$^3$ |

EXAMPLE 25

$^1$H NM Binding Studies

An 0.0132 M solution of 1c in CD$_2$Cl$_2$-acetone-$d_6$ (2:1, v:v) was prepared. A portion (0.75 mL) of this solution was transferred to an NMR tube; to the remainder of the solution was added Bu$_4$N$^+$H$_2$PO$_4^-$ such that its concentration was 0.189 M. A known volume of the anion-containing solution was added to the NMR tube, the tube was inverted several times to mix the contents, and the chemical shift of the amide NH protons of 1c was determined using a 500 MHz instrument. This process was repeated until these protons ceased to move downfield. Procedures similar to the one above were also used to asses the binding of 1c to H$_2$PO$_4^-$ in CD$_2$Cl$_2$-DMSO-$d_6$ (2:1, v:v), and the binding of 1c to Cl$^{31}$ in DMSO-$d_6$. Binding constants were calculated using the non-linear curve fitting program WinEQNMR.[20]

The stoichiometry of 1c+H$_2$PO$_4^-$ complexation in the NMR concentration regime was determined by the method of continuous variations (i.e., a Job analysis). Thus, equimolar solutions of 1c and Bu$_4$N$^+$H$_2$PO$_4^-$ were prepared (in CD$_2$Cl$_2$-acetone-$d_6$(2:1, v:v)), and were mixed in varying ratios in a series of NMR tubes such that the total number of mole of 1c+H$_2$PO$_4^-$ was the same in each tube. The chemical shift of the amide NH protons of 1c was recorded for each sample. A plot of {(δ$_{obs}$–δ$_0$)/δ$_{max}$}[1c ] vs. mole fraction 1c was then generated; it displayed a maximum at a mole fraction 1c of 0.65.

The foregoing is illustrative of the present invention, and is not to be construed as limiting thereof. The invention is defined by the following claim, with equivalents of the claims to be included therein.

The invention claim is:

1. A method of binding an anion, comprising contacting an anion to a compound of Formula I so that said anion is bound thereto:

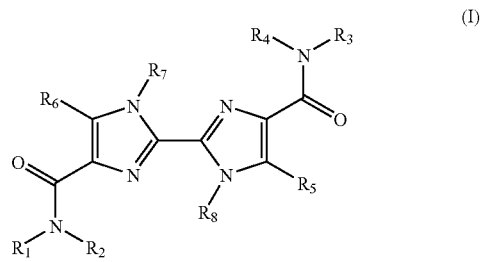

wherein:

R$_1$, R$_2$, R$_3$ and R$_4$ are each independently H, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, alkoxy, substituted alkoxy, arylalkenyl, substituted arylalkenyl, arylalkynyl, substituted arylalkynyl, aroyl, acyl, heterocyclic, substituted heterocyclic, halogen, cyano, nitro, macrocyclic ligand, and lipophilic groups;

R$_5$ and R$_6$ are each independently H, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, alkoxy, substituted alkoxy, arylalkenyl, substituted arylalkenyl, arylalkynyl, substituted arylalkynyl, aroyl, acyl, heterocyclic, substituted heterocyclic, halogen, cyano, nitro, or a macrocyclic ligand; and R$_7$ and R$_8$ are each independently H or lower alkyl.

2. The method of claim 1, wherein at least one of R$_1$, R$_2$, R$_3$ and R$_4$ is a macrocyclic ligand.

3. The method of claim 1, wherein at least one of R$_1$, R$_2$, R$_3$ and R$_4$ is a lipophilic group.

4. The method of claim 1 wherein said compound of Formula I is immobilized on a solid support.

5. The method of claim 1, wherein said anion is sulfate.

* * * * *